(12) United States Patent
Blackburn et al.

(10) Patent No.: US 10,335,468 B2
(45) Date of Patent: *Jul. 2, 2019

(54) IMMUNOTHERAPEUTIC COMPOSITIONS FOR THE TREATMENT OF ALZHEIMER'S DISEASE

(71) Applicant: MERCIA PHARMA, INC., New York, NY (US)

(72) Inventors: Peter Blackburn, New York, NY (US); Stephen Grimes, New York, NY (US)

(73) Assignee: MERCIA PHARMA, INC., New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/294,618

(22) Filed: Oct. 14, 2016

(65) Prior Publication Data

US 2017/0106063 A1 Apr. 20, 2017

Related U.S. Application Data

(63) Continuation of application No. 13/057,952, filed as application No. PCT/US2009/004504 on Aug. 6, 2009, now Pat. No. 9,498,522.

(60) Provisional application No. 61/086,938, filed on Aug. 7, 2008.

(51) Int. Cl.
  *C07K 14/47* (2006.01)
  *A61K 39/00* (2006.01)

(52) U.S. Cl.
  CPC .............. *A61K 39/0007* (2013.01); *A61K 2039/55566* (2013.01); *A61K 2039/57* (2013.01); *A61K 2039/6037* (2013.01); *A61K 2039/6081* (2013.01); *C07K 14/4711* (2013.01); *Y02A 50/466* (2018.01)

(58) Field of Classification Search
  CPC ...... A61K 39/0007; A61K 2039/55566; A61K 2039/6037; A61K 2039/6087
  See application file for complete search history.

(56) References Cited

U.S. PATENT DOCUMENTS

| 5,468,494 | A | 11/1995 | Gevas et al. |
| 5,688,506 | A | 11/1997 | Grimes et al. |
| 9,498,522 | B2 | 11/2016 | Blackburn et al. |
| 2004/0156820 | A1 | 8/2004 | Hagen |
| 2004/0247612 | A1 | 12/2004 | Wang et al. |
| 2007/0025959 | A1 | 2/2007 | Hagen |
| 2011/0206742 | A1 | 8/2011 | Blackburn et al. |

FOREIGN PATENT DOCUMENTS

WO WO 2002/038177 A2 5/2003

OTHER PUBLICATIONS

Lefeber DJ et al. Th1-directing adjuvants increase the immunogenicity of oligosaccharide-protein conjugate vaccines related to *Streptococcus pneumoniae* type 3. Infection & Immunity, 71(12):6915-6920. (Year: 2003).*
Vickers JC. A vaccine against Alzheimer's disease: Developments to date. Drugs Aging, 19(7):487-494. (Year: 2002).*
Agadjanyan "Prototype Alzheimer's disease vaccine using the immunodominant B cell epitope from beta-amyloid and promiscuous T cell epitopde pan HLA DR-binding peptide," J Immunol., 2005, 174:1580-1586.
Aucouturier et al., "Adjuvants Designed for Veterinary and Human Vaccines," Vaccine, 2001, 19:2666-2672.
Aucouturier et al., "Montanide ISA 720 and 51: a new generation of water in oil emulsions as adjuvants for human vaccines," Expert Rev. Vaccines, 2002, 1(1):111-118.
Conroy et al., "Mercia Adjuvant System 1 (MAS-1)—an effective water-in-oil adjuvant for vaccines," Abstract from poster session #27, Modern Vaccines Adjuvants & Delivery Systems (MVADS) Meeting, Sep. 12-14, 2006, The Royal Society of Medicine, London, UK.
Fox, "Squalene emulsions for parenteral vaccine and drug delivery," Molecules, 2009, 14:3286-3312.
Geylis et al., "Human Monoclonal Antibodies Against Amyloid-Beta from Healthy Adults," Neurobiology of Aging, 2005, 26:597-606, doi: 10.1016/j.neurobiolaging.2004.06.008.
Ghochikyan et al., "Prototype Alzheimer's Disease Epitope Vaccine Induced Strong Th2-Type Anti-A-Antibody Response with Alum to Quil A Adjuvant Switch," Vaccine, 2006, 24(13):2275-2282.
International Search Report for International Application No. PCT/US2009/004504, prepared by the International Search Authority, dated Apr. 29, 2010, 2 pages.
Jin et al., "Induction of potent cellular immune response in mice by hepatitis C virus Ns3 protein with double-stranded RNA," Immunology, 2007, 122:15-27.
Lemere et al., "Amyloid-beta immunotherapy for the prevention and treatment of Alzheimer disease: Lessions from mice, monkeys, and humans," Rejuvenation Res., 2006, 9(1):77-84.
Liu et al., "MER5101, A Novel A-15:DT Conjugate Vaccine, Generates a Robust Anti- A-Antibody Response and Attenuates A Pathology and Cognitive Deficits in APPswe/PS1L1E9 Transgenic Mice," The Journal of Neuroscience, 2013, 33(16):7027-7037, doi:10.1523/JNEUROSCI.5294-12.2013.
Maier et al., "Short amyloid-beta (Abeta) immunogens reduce cerebral Abeta load and learning deficits in an Alzheimer's disease mouse model in the absence of an Abeta-specific cellular immune response," J Neurosci., 2006, 26(18):4717-4728.
Mandokhot et al., "Humoral Hyporesponsiveness to a Conjugate Contraceptive Vaccine and its Bypass by Diverse Carriers Using Permissible Adjuvant," Clin. Exp. Immunol., 2000, 122(1):101-108.
Mercia Pharma, "Adjuvant systems," 2005. [Date retrieved: Apr. 21, 2010]. merciapharma.com/adjuvant.html.

(Continued)

*Primary Examiner* — Kimberly Ballard
(74) *Attorney, Agent, or Firm* — Hoxie & Associates LLC

(57) ABSTRACT

A safe and effective vaccine to prevent, slow, halt or reverse progression of Alzheimer's disease in human patients is disclosed. The vaccine includes Aβ1-42 or an beta amyloid self epitope (e.g. Aβ1-15, or other 7-mer or 15-mer peptide epitopes derived from Aβ1-42) conjugated to an immunogenic carrier (e.g. DT) formulated in a water-in-oil Th2-biased adjuvant/delivery system.

11 Claims, 10 Drawing Sheets

Specification includes a Sequence Listing.

(56) References Cited

OTHER PUBLICATIONS

Osherovich, "AD Vaccine Redux," SciBX (Science-Business eXchange), 2013, 6(18):8-18.

Singh et al., "Synthesis and characterization of hapten-protein conjugates for antibody production against small molecules," Bioconjugate Chem., 2004, 15:168-173.

Wang et al., "Site-specific UBITh® Amyloid-Beta Vaccine for Immunotherapy of Alzheimer's Disease," Vaccine, 2007, 25(16): 3041-3052, doi: 10.1016/j.vaccine.2007.01.031.

Wilcock et al., "Immunotherapy, vascular pathology, and microhemorrhages in transgenic mice"CNS Neurol Disord Drug Targets., 2009, 8(1):50-64.

Yang et al., "Directly Synthesize $Aß_{1-5}$ Peptide Vaccine by Fmoc Solid-Phase Peptide Synthesis and Study Its Immune Activity", Journal of Sun Yat-Sen University (Medical Sciences), 2006, 27(2): 121-125 (with English Abstract).

Zakaib, "Aß Vaccine Leads to Safer Immune Response in Mice", Alzheimer Research Forum (web article), Apr. 25, 2013, www.alzforum.org/new/detail.asp?id=3472.

* cited by examiner

FIG. 1A and B: Anti-Aβ1-42 antibody levels and Ig isotypes in plasma following immunization
A)
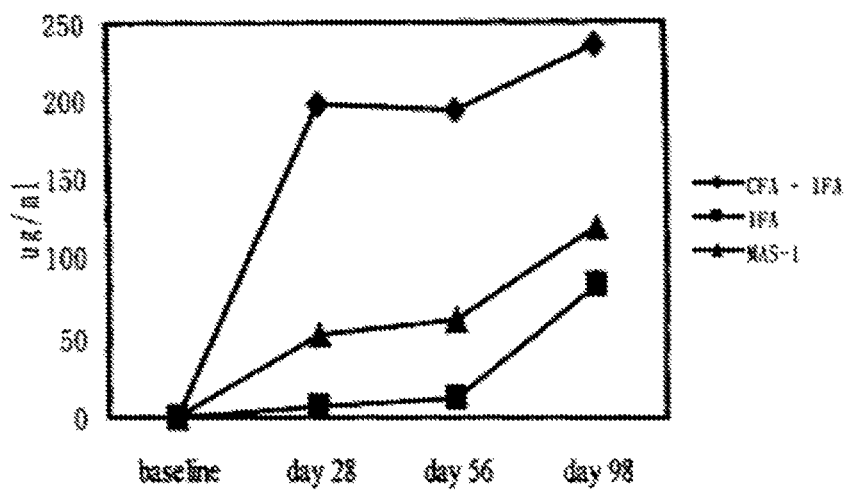
B)
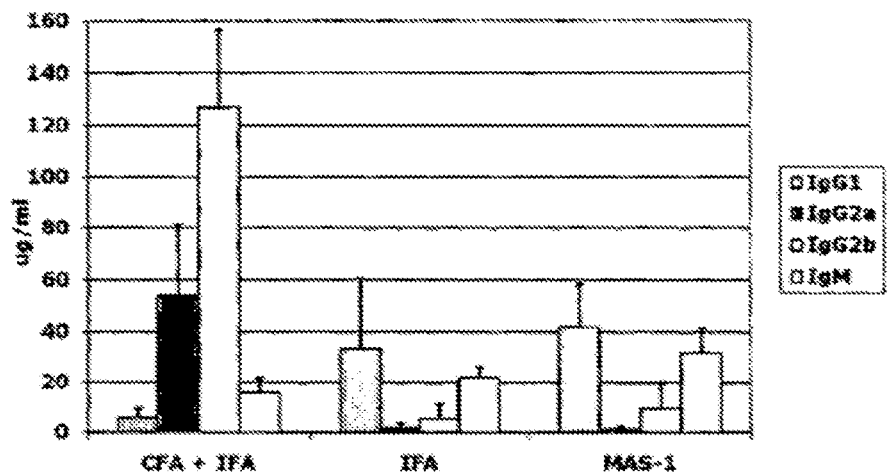

FIG. 2: Binding of plasma from the mice immunized with full length Aβ in CFA/IFA, IFA and MAS-1 to Aβ plaques in sections of brain from APP Tg mice.
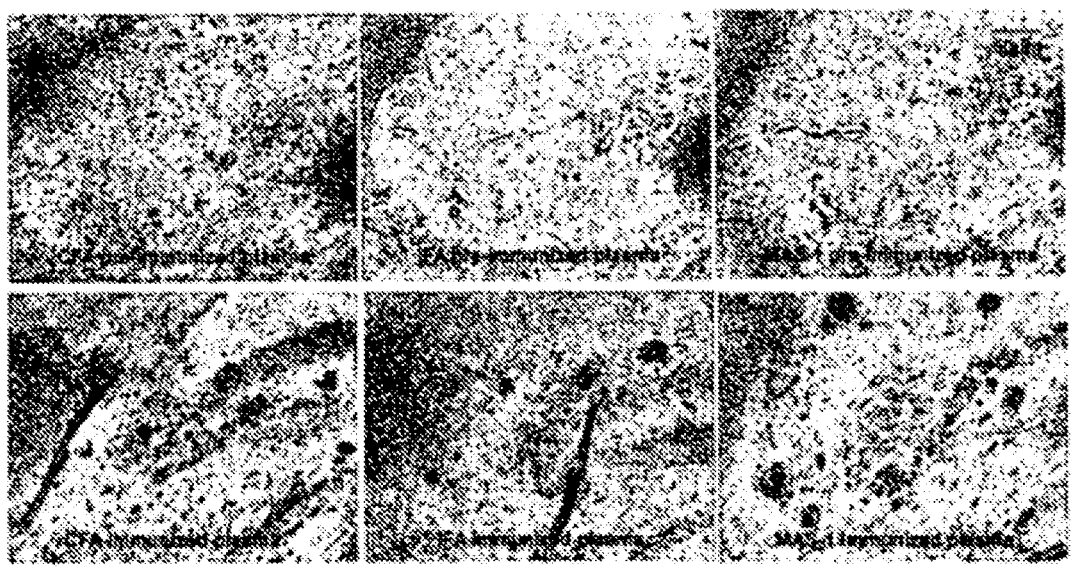
Anti-Aβ immunoreactivity of APP transgenic mouse AD plaques

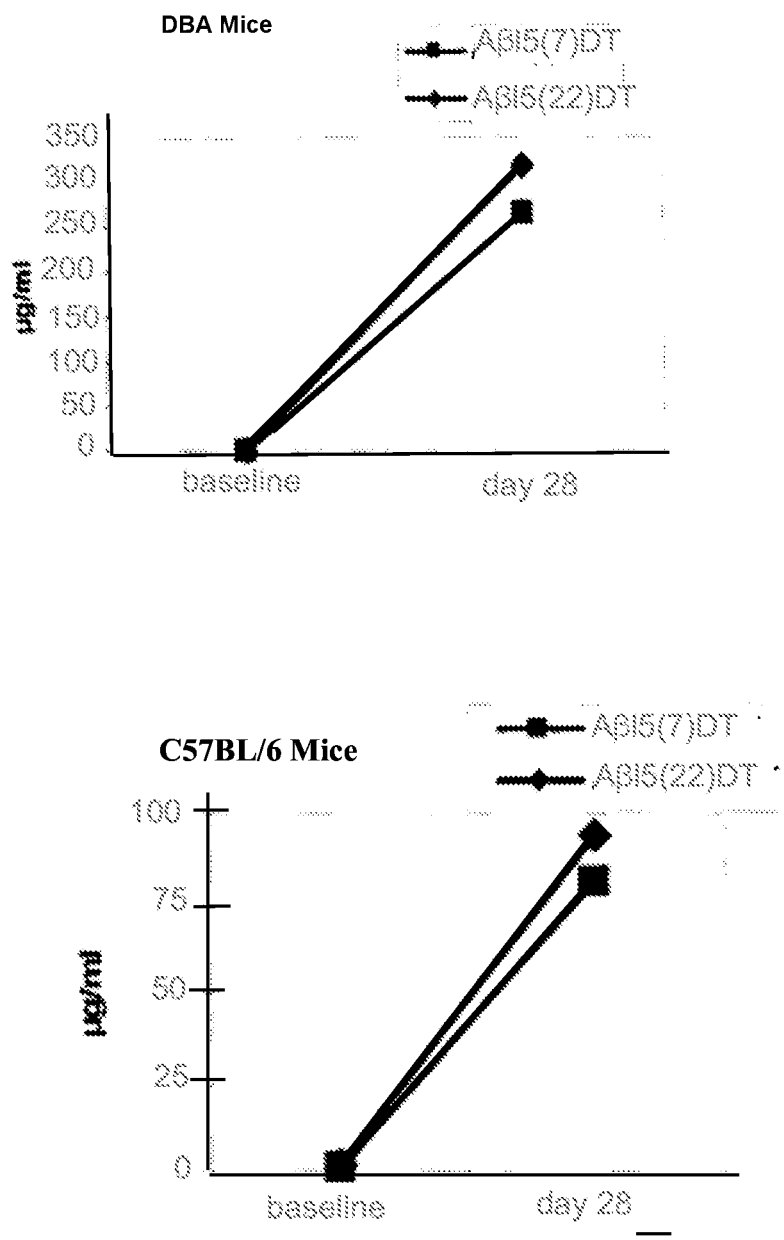
FIG. 3: Immunopotency in mice of Aβl5(7)DT and Aβl5(22)DT formulated in MAS-1

Fig 4. Immunopotency in DBA and B6 mice of Aβ15($_7$)DT, Aβ15($_{22}$)DT, and Aβ 42 in MAS-1
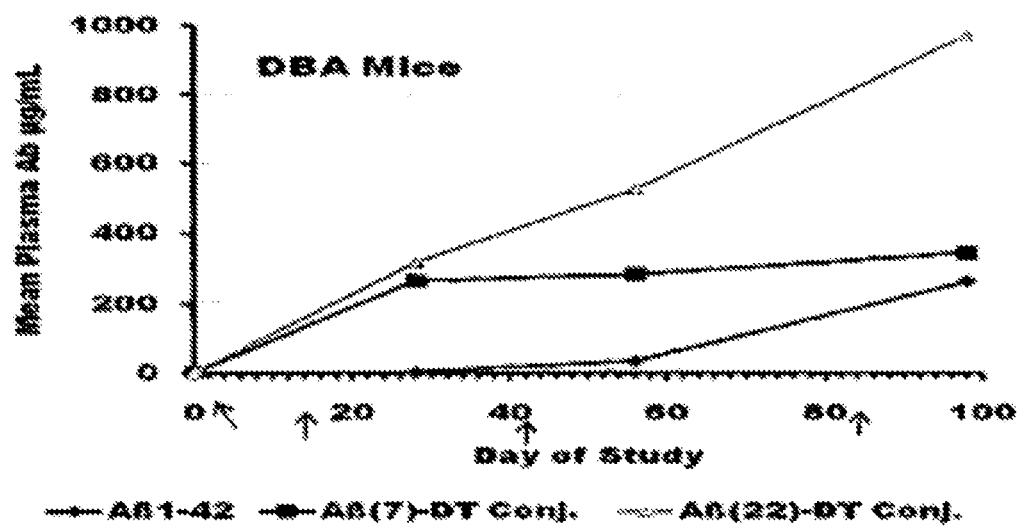
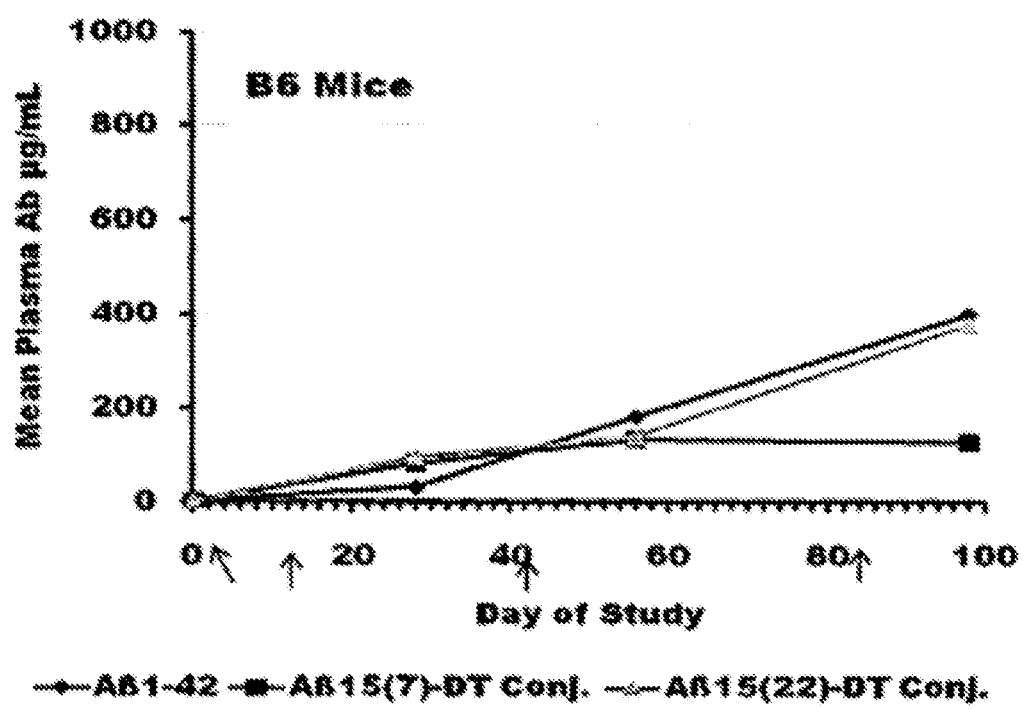

FIG. 5 Anti-Aβ isotypes in C57BL/6 mice induced by Aβ15(7)DT and Aβ15(22)D Aβ1-42 in MAS-1
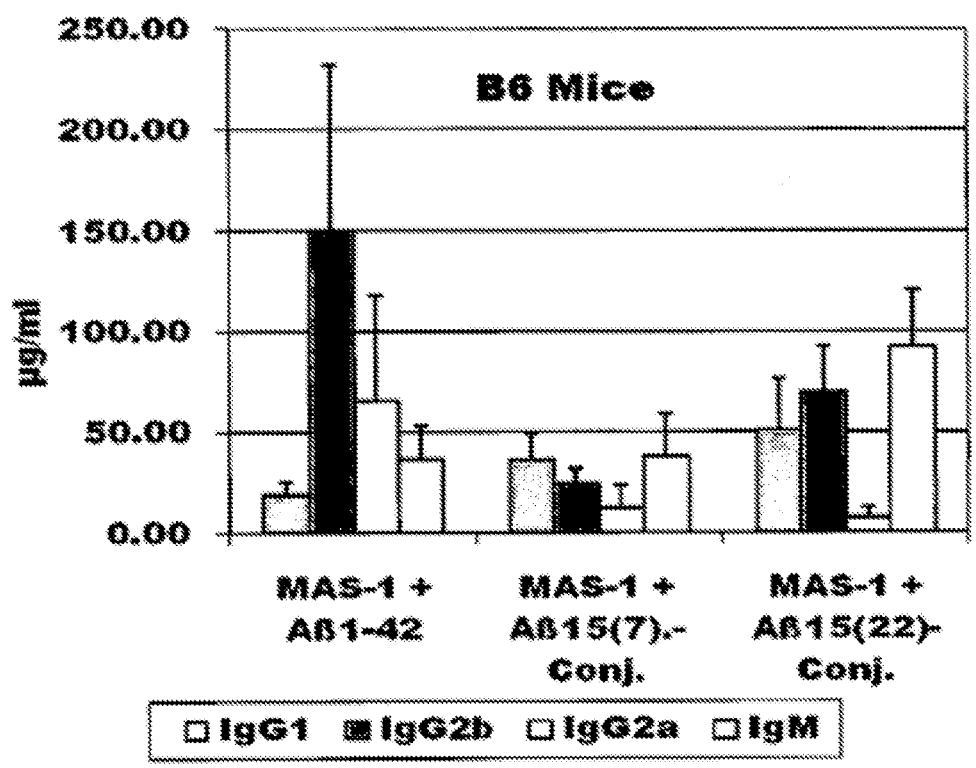

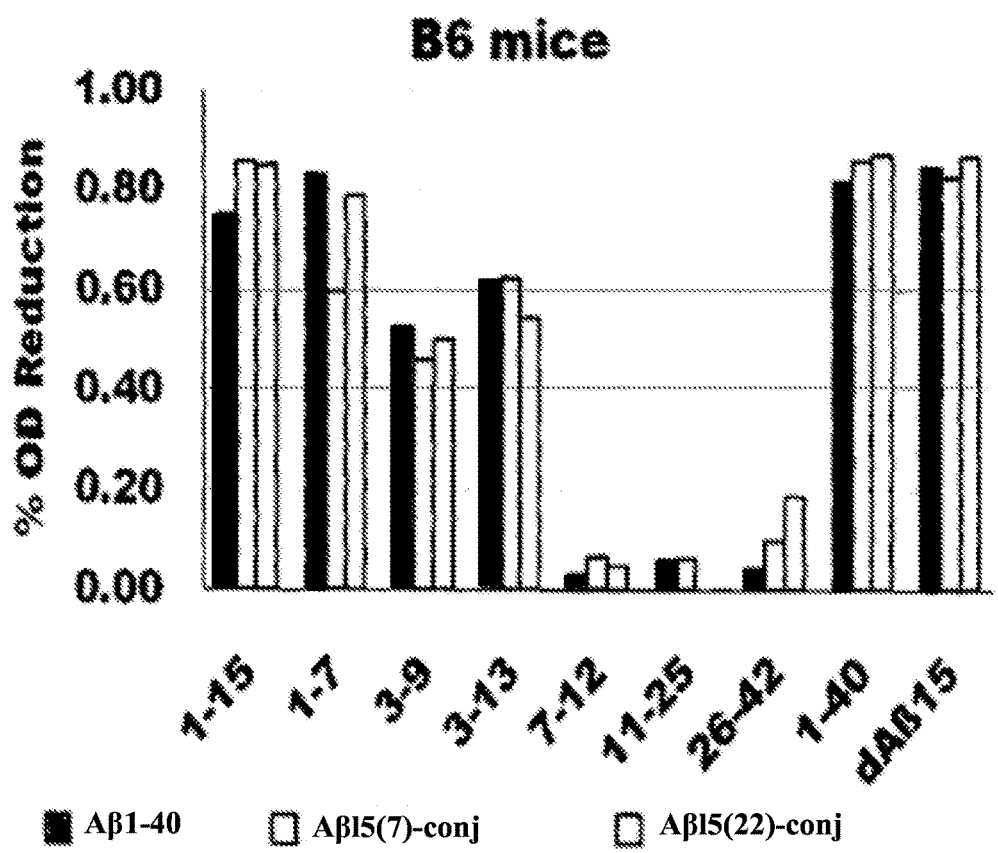
FIG. 6 Epitope mapping of anti-Aβ specifity induced by Aβ1-42, Aβ15(7)DT, and Aβ15(22)DT in Aβ1-42 in MAS-1

FIG. 7 Anti-Aβ immunoreactivity to Human AD plaques by plasma from DBA mice immunized with Anti-Aβ1-42, Aβ15(7)DT, and Aβ15(22)DT in MAS-1
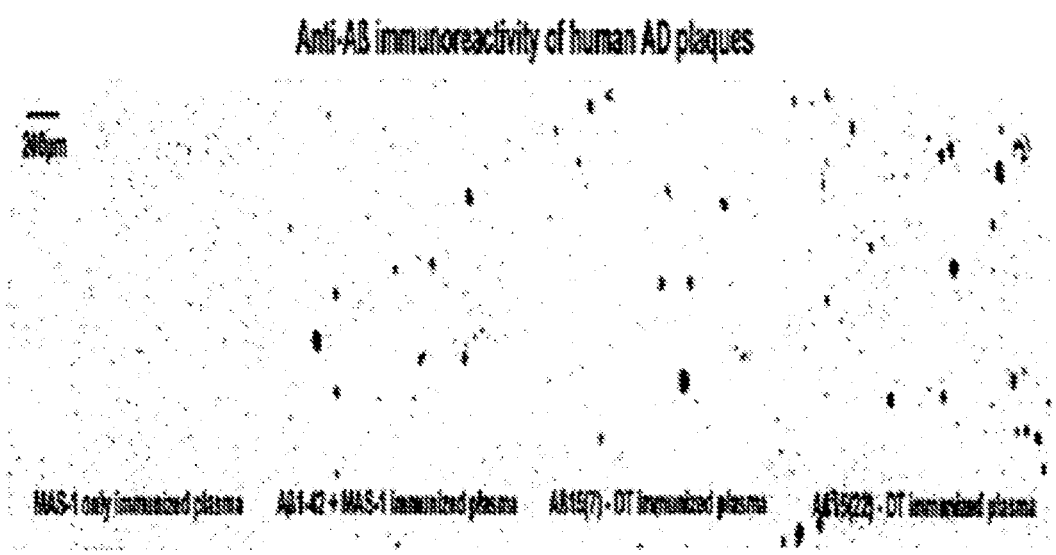

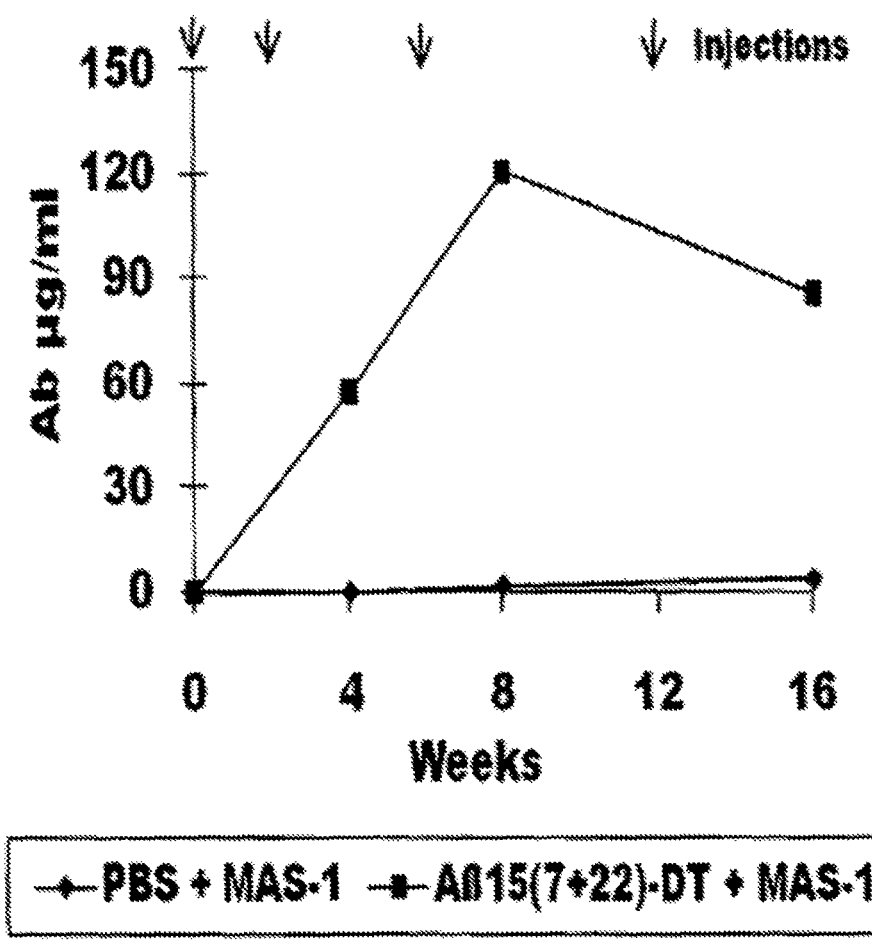
FIG. 8. Anti-Aβ levels in 3xTg-AD mice

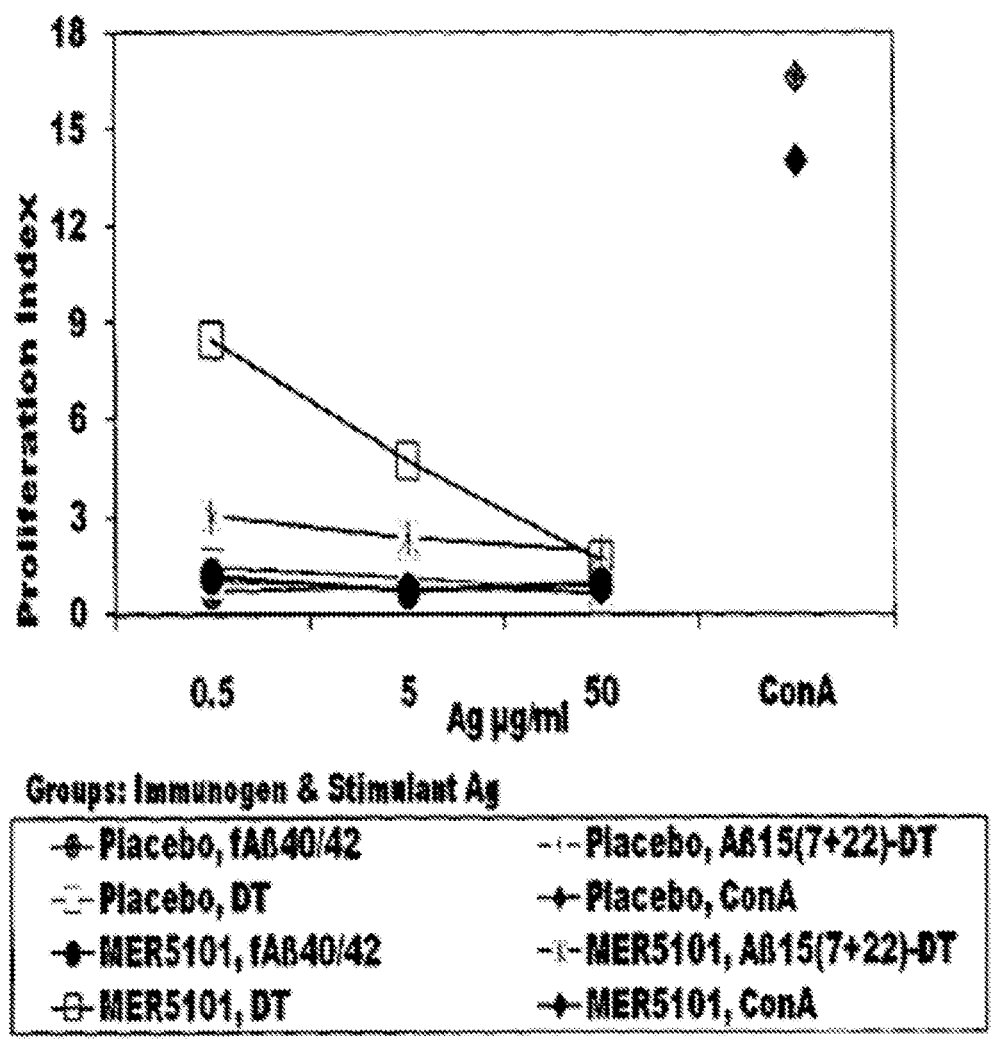
FIG. 9 Splenocyte stimulation assay

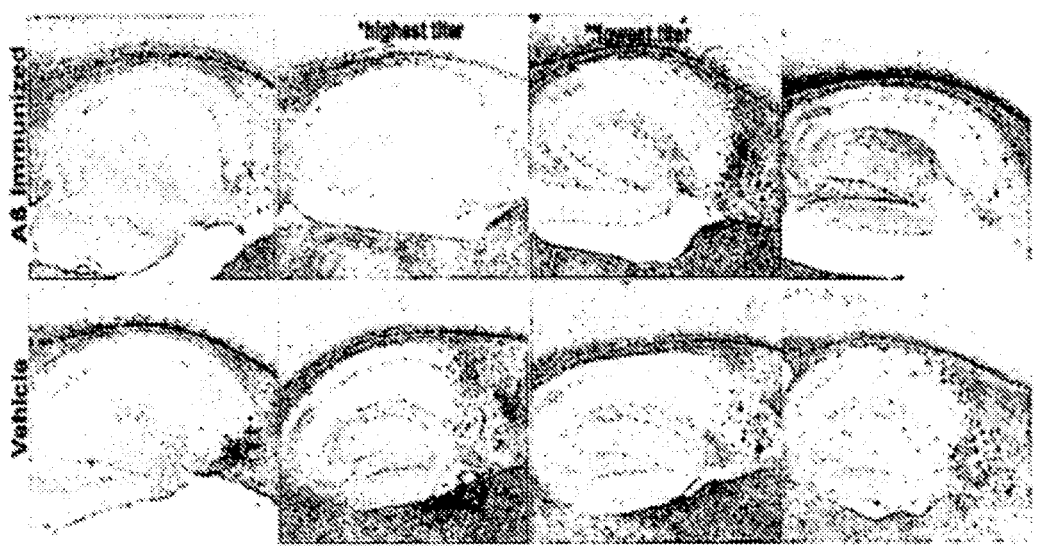
FIG. 10: Brain Sections from each 3xTg-AD Mouse stained for Aβ plaque

IMMUNOTHERAPEUTIC COMPOSITIONS FOR THE TREATMENT OF ALZHEIMER'S DISEASE

REFERENCE TO RELATED APPLICATIONS

This application is a continuation application of U.S. application Ser. No. 13/057,952, filed Feb. 7, 2011, which is a United States National Stage Application under 35 USC § 371 of PCT/US2009/004504, filed Aug. 6, 2009, which claims the benefit of the filing date of U.S. Provisional Application Ser. No. 61/086,938, filed Aug. 7, 2008, the disclosure of which is hereby incorporated by reference.

FIELD OF THE INVENTION

The field relates to a safe and efficacious vaccine to prevent, slow, halt or reverse progression of Alzheimer's disease (AD). AD is characterized by the deposition of amyloid β (Aβ) deposits in the brain. Clearance of Aβ by Aβ1-42 vaccination (AN1792) has shown promise clinically, but suffered from limiting inflammatory effects in a subset of patients. Self antigens like Aβ are poorly immunogenic, requiring potent adjuvants such as the QS21, a saponin used in AN1792 vaccine, which induce Th1 biased responses. Alum, an approved Th2 biased adjuvant, acts poorly with self antigens.

BACKGROUND OF THE INVENTION

Alzheimer's disease (AD) is a neurodegenerative disorder characterized by a progressive loss of cognitive function and is the most frequent type of dementia in the elderly, affecting almost half of all patients with dementia.

Correspondingly, advancing age is the primary risk factor for AD. Among people aged 65, 2-3% show signs of the disease, while 25-50% of people aged 85 have symptoms of AD and an even greater number have some of the pathological hallmarks of the disease without the characteristic symptoms. Every five years after the age of 65, the probability of having the disease doubles. The share of AD over the age of 85 is the fastest growing segment of the AD population in the US, although current estimates suggest the 75-84 year-old population has about the same number of patients as the over 85 population (Herbert at al., 2003). The Alzheimer's Association recently reported that there are more than 5 million people in the US living with AD (Alzheimer's Association, 2007). This number is expected to triple by the year 2050.

The current cost to government agencies of the care of patients who have AD is substantial, and it is rising rapidly: By 2010, Medicare spending on AD is expected to grow to $49.3 billion (a 54% increase over the costs in 2000), and Medicaid spending will grow to $33 billion (an 80 percent increase over costs in 2000). AD has been reported to cost American businesses $61 billion annually. Of that amount, the annual cost attributable to lost productivity and replacement costs when workers become caregivers for a relative who has AD is an estimated $36.5 billion. These costs reflect neither the direct financial costs to family caregivers (e.g., lost income) nor the costs associated with depression among family members providing end-of-life care (Prigerson, 2003). There is currently no cure for AD and available medications offer relatively small symptomatic benefit for some patients but do not slow disease progression.

AD is characterized by the deposition of cerebral amyloid-β (Aβ) protein, neuritic plaques, glial cell activation, and neurofibrillary tangles composed of hyperphosphorylated tau protein (Selkoe, 2001). Epidemiologic, pathologic, and genetic evidence demonstrates that Aβ has a pivotal role in the pathogenesis of AD (Golde, 2003). Immunization of amyloid precursor protein (APP) transgenic mice with aggregated Aβ1-42 peptide in Freund's adjuvant injected intraperitoneally resulted in the lowering of cerebral Aβ (Schenk et al., 1999). Reduced cerebral Aβ levels in PDAPP-tg mice following intranasal immunization with Aβ1-40 peptide have also been reported (Lemere et al., 2000; Weiner et al., 2000). Soon thereafter, several reports demonstrated the importance of antibody-mediated clearance of Aβ and its role in improving cognition (Bard et al., 2000; Janus et al., 2000; Morgan et al., 2000; Dodart et al., 2002). In addition, anti-Aβ antibodies have been induced following immunization with Aβ using various adjuvants (Lemere et al., 2002; Cribbs et al., 2003; Lemere et al., 2000, 2002, 2003; Spooner et al., 2002: Maier et al., 2005; Ghochikyan et al., 2006) and by DNA immunization (Ghochikyan et al., 2003, Zhang et al., 2003, Okura et al., 2006, Frazer et al, 2007). In addition to an active immunization strategy, passive immunization with antibodies against Aβ have also been shown to remove Aβ from the brain and is associated with an improvement in cognitive function in a mouse model of AD (Bard et al., 2000, DeMattos et al., 2001). Together these encouraging animal data led to a multi-center Aβ vaccine (AN1792) clinical trial (Schenk, 2002; Orgogozo et al., 2003; Gilman et al., 2005).

The AN1792 vaccine was deficient in two respects. First, AN1792 induced an effective immune response in only 59 of 300 treated patients (19.7%) and, secondly, the clinical trial had to be halted when 18 (6%) of the treated subjects experienced symptoms of meningoencephalitis (Schenk, 2002; Orgogozo et al., 2003; Gilman et al., 2005). Autopsy case reports from subjects who received AN1792 vaccination demonstrated regions with strongly reduced numbers of plaques compared to controls (Nicoll et al., 2003; Ferrer et al., 2004; Masliah et al., 2005). However, T cell infiltrates, (primarily $CD4^+$ with fewer $CD8^+$ cells) were present in the leptomeninges, perivascular spaces, and brain parenchyma in two cases, suggesting a T cell-mediated immune response to AN1792 vaccination. Although no neuroinflammation was observed in pre-clinical studies a recent report had shown that immunization of C57BL/6 mice with Aβ and pertussis toxin induces autoimmune meningoencephalitis with characteristics similar to those observed in humans immunized with AN1792 (Furlan et al., 2003). Follow up studies on the AN1792 trial showed that AD patients that developed antibodies that bound to Aβ plaques showed significantly slower rates of decline in cognitive function. These findings suggest that the generation of anti-Aβ antibodies by active immunization is a promising immunotherapeutic approach for AD provided that a robust immune response can be elicited in these elderly patients, and that excessive cell mediated immune reactions are minimized in order to avoid unwanted neuroinflammation. The exact mechanism by which Aβ antibodies reduce Aβ burden in the brain is not known but hypotheses include Fc-receptor mediated phagocytosis via microglia, dissolution of amyloid fibrils, or sequestration of circulating Aβ resulting in an increased net efflux of Aβ from the brain (Vasilevko and Cribbs, 2006). Clearly, whatever the mechanism, immunotherapy, either active or passive, has the potential to clear Aβ in AD and improve cognitive function.

Active immunization schedules are being developed to minimize T lymphocyte-mediated immune reactions and to maximize antibody production. The B cell epitope(s) in humans (Geylis et al., 2005), monkeys (Lemere et al., 2004) and mice (Lemere et al., 2000; McLaurin, et al., 2002; Agadjanyan et al., 2005) is located within the Aβ1-15 region, while the T cell epitope has been mapped within Aβ15-42 (Cribbs et al., 2003; Monsonego et al., 2003). Thus, Aβ fragments spanning the B cell epitope but not the T cell epitopes may be safer immunogens to potentially avoid deleterious anti-Aβ cellular immune responses. Many approaches to enhance immunogenicity of these shorter Aβ fragments have been studied such as conjugation of the B cell epitope, Aβ1-15 to the universal helper T cell epitope, PADRE (Agadjanyan et al., 2005; Ghochikyan et al., 2006), expansion with the addition of lysine residues and glutamate substitutions to reduce β-sheet content (Siguardsson et al., 2001, 2004) or presentation as multiple copies (Zhou et al., 2005). More recently an UBITh® AD immunotherapeutic vaccine has been described whereby the intrinsic self Th epitopes of Aβ1-42 are replaced with foreign UBITh® epitopes (Wang et al., 2007). Results from a repeat dose toxicity study in macaques have shown no evidence for immunotoxicity or overall toxicity following immunization with this Aβ1-14 UBITh® vaccine.

The dendrimeric Aβ1-15 (dAβ1-15), composed of 16 copies of Aβ1-15 on a branched lysine core which includes an Aβ-specific B cell epitope but lacks the T-cell epitope, is an effective immunogen. Immunization intranasally (i.n.) with dAβ1-15, using an experimental adjuvant LT (R192G), mutant *E. coli* heat-labile enterotoxin (Dickinson and Clements, 1995), resulted in a robust humoral immune response with a significant reduction in cerebral plaque burden in J20 APP-tg mice (Seabrook et al., 2006). When injected s.c. in mice dAβ1-15, with LT (R192G) adjuvant, induced a humoral immune response with anti-Aβ antibodies, principally of the IgG1 isotype with lower levels of IgG2a and IgG2b, which bound cerebral Aβ plaques in brain tissue from an AD patient (Seabrook et al., 2006). In another study, the i.n. immunization with a tandem repeat of two lysine-linked Aβ1-15 sequences (2× Aβ1-15) using LT (R192G) adjuvant reduced cerebral Aβ load and learning deficits in hAPP mice in the absence of an Aβ-specific cellular immune response (Maier et al., 2006).

In addition to using short Aβ derivatives that have less intrinsic neurotoxicity, adjuvants which can direct the immune response towards a Th2 phenotype may also be critical for the design of a safe, immunogenically robust, and efficacious vaccine for AD (Cribbs et al., 2003; Ghochikyan et al., 2006). QS21, an adjuvant known to induce a strong Th1 humoral response (IgG2a antibodies in mice) was used in the AN1792 trial, and may have contributed to the T cell mediated inflammation observed during its clinical evaluation. Many studies in animals to date focused on getting a good antibody titer by using strong adjuvants, such as CFA/IFA, that give a mixed Th1/Th2 immune response. It has been shown that Aβ1-15 in tandem with the universal helper T cell epitope (PADRE), PADRE Aβ1-15-MAP when formulated in alum, a Th2 biased adjuvant, generated mainly IgG1 antibody isotypes, but gave a less robust immune response than when formulated in Quil A, a Th1 biased adjuvant generating predominantly IgG2a isotypes (Ghochikyan et al., 2006). Although robust Th-2 type humoral responses to Aβ following subcutaneous or intramuscular routes have not been reported, the Th2-type humoral response in APP/TG mice following intranasal vaccination with Aβ peptide using LT (R192G) adjuvant was associated with significant decreases in the cerebral Aβ plaque burden, decreased local microglial and astrocytic activation, and reduced neuritic dystrophy (Weiner et al., 2000). Thus, in principle, an anti-Aβ vaccine that elicits a robust Th2 biased immune response in the AD population should be efficacious for treatment of AD.

SUMMARY OF THE INVENTION

Anti-Aβ vaccines that induce a robust Th2 biased immune response while avoiding deleterious inflammatory Th1 biased cellular immune responses may be efficacious for treatment of AD. Aβ1-42 in an appropriate adjuvant may also achieve this result. In addition, B cell-specific short Aβ peptide epitopes lacking Th1 epitopes are promising candidates for an effective immunotherapy regime for AD by avoiding potentially deleterious inflammatory cellular immune responses. However, such peptide self epitopes require additional T cell help, and additionally require a strong Th2 biased adjuvant to drive the desired immune response and generate high titers of anti-Aβ antibodies in humans. The invention provides Aβ peptide epitopes such as Aβ1-42 in a water-in-oil emulsion type Th2-biased adjuvant/delivery system to avoid or suppress Th1 biased cell mediated inflammation. One embodiment of the invention concerns the self epitope (Aβ1-15) that lacks the Th1 epitope, conjugated to an immunogenic carrier (DT) to form Aβ15DT conjugate, which is then formulated in a water-in-oil emulsion adjuvant/delivery system to induce a Th2 biased immune response. The immunogenic compositions may be administered to patients by subcutaneous or intramuscular injection in one example.

The disclosed immunotherapeutic compositions relate to immunogens comprised of Aβ 1-42, or amino acid residues derived therefrom, including amino acid residues 1-15 of Aβ coupled via a C-terminal peptide spacer to an immunogenic carrier, such as diphtheria toxoid (DT—a component of approved childhood and adult vaccines), formulated in a water-in-oil emulsion type adjuvant. The compositions are designed to induce neutralizing neutralizing antibodies against AB while avoiding Th1 based cytotoxic T cell mediated inflammation.

BRIEF DESCRIPTION OF THE FIGURES

FIGS. 1A and B depict anti-Aβ1-42 antibody levels and Ig isotypes in plasma following immunization.

FIG. 2 shows binding of plasma from the mice immunized with Aβ1-42 in CFA/IFA, IFA, or MAS-1 adjuvants to Aβ plaques in sections of brain from APP Tg mice.

FIG. 3 shows an immunopotency in mice of Aβ15$_{(7)}$DT and Aβ15$_{(22)}$DT conjugates at peptide-to-carrier substitution ratios of 7 and 22, respectively, formulated in MAS-1.

FIG. 4 shows an immunopotency in mice of Aβ15$_{(7)}$DT and Aβ15$_{(22)}$DT conjugates at peptide-to-carrier substitution ratios of 7 and 22, respectively, formulated in MAS-1.

FIG. 5 depicts anti-Aβ isotypes in C57BL/6 mice induced by Aβ1-42, Aβ15$_{(7)}$DT, and Aβ15$_{(22)}$DT in MAS-1.

FIG. 6 shows an epitope mapping of anti-Aβ specificity induced by Aβ1-42, Aβ15$_{(7)}$DT, and Aβ15$_{(22)}$DT in MAS-1.

FIG. 7 shows comparable anti-Aβ Immunoreactivity to Human AD plaques by plasma from DBA mice immunized with Anti-Aβ1-42, Aβ15$_{(7)}$DT, and Aβ15$_{(22)}$DT in MAS-1.

FIG. 8 depicts Anti-Aβ levels in 3×Tg-AD mice.

FIG. 9 shows a splenocyte stimulation assay.

FIG. 10 depicts brain sections from each 3×Tg-AD Mouse stained for Aβ plaque.

DETAILED DESCRIPTION

The examples and drawings provided in the detailed description are merely examples, which should not be used to limit the scope of the claims in any claim construction or interpretation.

AD Therapeutic Vaccines

Conjugation of small molecules, including peptides, to immunogenic carriers such as DT is an established means of enhancing their immunogenicity. However, to render self antigen conjugates strongly immunogenic in humans also requires formulation with a suitable adjuvant. MAS-1, is a water-in-oil emulsion adjuvant system comprising mannide monooleate, squalene and squalane available from Mercia Pharma, Inc. MAS-I was developed for use in humans with self antigen conjugate constructs to produce therapeutic vaccines that stimulate sustained neutralizing antibody responses to self antigens without inducing cell-mediated cytotoxicty or breaking immune self tolerance against the self component of the vaccine, and that are well tolerated and without systemic toxicity.

Mannide monooleate based adjuvants are commercially available, such as Incomplete Freund's Adjuvant (IFA) from a number of sources, and ISA 51 and ISA 720 available from SEPPIC, Paris, France. Water-in-oil type emulsion adjuvants may also be formulated with mannide monooleate which is commercially available from a number of sources (such as Combe, Inc. under the tradename, Arlacel), and squalene and squalane (from several commercial sources). The water-in-oil adjuvants used in the disclosed compositions may be formulated so that the aqueous globules in the emulsion carrying the antigen have median diameters less than 1 micron with median diameters in the range from about 100 nanometers to about 1 micron, and typically with an average diameter of about 300 nanometers. The oil components of MAS-1 are naturally occurring biological oils that are metabolizable, unlike the mineral oil that comprises the oil phase of the well known Freund's adjuvants (both incomplete and complete formulations).

A number of carrier proteins such as, but not limited to, diphtheria toxoid (DT), CRM197 (Wyeth)—a mutant form of DT, tetanus toxoid (TT) and keyhole limpet hemocyanin (KLH), may be used in the compositions of the invention. DT is a preferred carrier protein because it is approved for use in childhood and adult vaccines with an excellent safety record and is produced in quantity to cGMP by a number of commercial sources.

Specificity of the Adjuvant/Delivery System

For decades, Freund's adjuvant emulsions (CFA/IFA) have been standards against which other adjuvants have been measured. CFA is not suitable for use in humans, due especially to the intense inflammatory reactions induced by its mycobacterium component; although, IFA has been used in clinical trials, it has never been approved for any human indications. Nevertheless, these water-in oil (W/O) emulsions are generally recognized as potent adjuvants and are used widely in animal studies.

Alum is the only currently U.S.-approved adjuvant with a Th2 bias avoiding cell mediated cytotoxicity, but alum is inadequate as an adjuvant for self-epitope conjugate vaccines due to insufficient immunopotency. IFA type adjuvants such as ISA 51, which are mineral oil based, have a drawback as an adjuvant for repeat use in treating chronic disease settings because IFA's mineral oil deposits remain at injection sites and can lead to formation of cysts.

MAS-1 adjuvant/delivery system was specifically developed to augment humoral responses to poorly immunogenic self-antigens in humans. MAS-1 adjuvant emulsions are significantly more potent than Alum and comparable or superior to IFA emulsions in terms of immunogenicity, but MAS-1 is significantly better tolerated than IFA after i.m or s.c. injection and has excellent pharmaceutical physicochemical characteristics. These include homogeneous globule size distribution for efficient antigen presentation, low viscosity to facilitate low volume doses, and extended stability at refrigerated temperatures facilitating distribution through standard cold chain procedures.

Unlike IFA, MAS-1 is comprised of natural and metabolizable components that provide a depot of vaccine and thereby promote prolonged efficient immunostimulation. MAS-1 is eventually cleared from the injection site. MAS-1 emulsions are robust, reproducible and stable whether made in bulk or as single units at point-of-use and may be produced in formulations with aqueous globules carrying the antigen having median diameters less than 1 micron, and typically about 300 nanometers. By contrast, IFA emulsions are administered in formulations that have aqueous globules of about 3 to 10, or even 50, microns in diameter with concomitant variability in emulsion stability, are highly viscous making small volume dosing and large scale bulk manufacture difficult.

Aβ1-42 Peptide Vaccine Formulated in MAS-I

The Aβ1-42 vaccine (AN1792) is formulated in a QS21 based adjuvant. QS21, a strong Th1 biased adjuvant, may have contributed to the inflammatory side effects of the AN1792 vaccine. Aβ1-42 formulated in MAS-I is evaluated for its capacity to promote a robust Th2 biased antibody response to amyloid plaque in brain tissue, while avoiding the generation of amyloid beta specific cell mediated immunity associated with a Th1 response.

FIGS. 1A and B depict anti-Aβ1-42 antibody levels and Ig isotypes in plasma following immunization:

1 (A) Female DBA mice are immunized s.c. with 100 ug Aβ1-42 on days 0, 14, 42 and 84 and anti-Aβ antibodies measured in plasma by ELISA at baseline, day 28, 56 and 98 and B) Ig isotypes at day 98.

Aβ1-40 and Aβ1-42 peptide antigens are synthesized by standard solid-phase peptide synthesis methodology. DBA2 mice (n=4) are injected subcutaneously (s.c.) with 100 μg Aβ (75 μg Aβ1-40 and 25 μg Aβ1-42) formulated in MAS-1, CFA/IFA, or IFA on days 0, 14, 42 and 84. Antibody titers in plasma are determined by ELISA on days 0, 28, 56 and 98. Results show that full length Aβ formulated in MAS-1 induces robust antibody titers superior to IFA at day 28, 56 and 98 (FIG. 1A).

Aβ1-40 and Aβ1-42 peptide antigens are synthesized by standard solid-phase peptide synthesis methodology. DBA2 mice (n=4) are injected subcutaneously (s.c.) with 100 μg Aβ (75 μg Aβ1-40 and 25 μg Aβ1-42) formulated in MAS-1, CFA/IFA, or IFA on days 0, 14, 42 and 84. Antibody titers in plasma are determined by ELISA on days 0, 28, 56 and 98. Results showed that full length AB formulated in MAS-1 induces robust antibody titers superior to IFA at day 28, 56 and 98 (FIG. 1A). Aβ1-42 in CFA/IFA (positive control), as expected, yielded a more rapid and initially higher antibody levels than either the MAS-1 or IFA formulations. The responses to both MAS-1 and IFA formulations increased throughout the study and had not reached a plateau at day 98 when the final blood sample was taken; Isotyping of the day 98 samples showed that CFA/IFA elicited a mixed Th1/Th2 immune response with significant titers of IgG2a and IgG2b antibodies, respectively. Whereas, the MAS-1 and IFA formulations elicited Th2 dominated responses, with IgG1 the predominant isotype along with IgM, low levels of IgG2b, and only very low levels of the Th-1 type IgG2a antibodies (FIG. 1B). Plasma from the mice immunized with full length Aβ1-42 in CFA/IFA, IFA, and MAS-1 showed equal levels of binding to human Aβ plaque in brain sections from APP Tg mice (FIG. 2), demonstrating that the Th-2 dominant antibody isotypes effectively recognized amyloid plaque indicating that the Th-2 biased vaccine has the potential to reduce amyloid plaque burden while avoiding Th-1 mediated toxicity.

FIG. 2 shows binding of plasma from the mice immunized with Aβ1-42 in CFA/IFA, IFA, or MAS-1 adjuvants to Aβ plaques in sections of brain from APP Tg mice. Plasma are taken at day 98 from mice immunized with Aβ1-42 in CFA/IFA, IFA, and MAS-1 on days 0, 14, 42 and 84 equally bound cerebral Aβ plaques in brain sections from APP Tg mice (lower panel). Pre-immune plasma is used as a control and did not bind cerebral Aβ plaques (upper panel).

Plasma from the mice immunized with full length Aβ1-42 in CFA/IFA, IFA, and MAS-1 show equal levels of binding to human Aβ plaque in brain sections from APP Tg mice (FIG. 2), demonstrating that the Th-2 dominant antibody isotypes effectively recognized amyloid plaque indicating that the Th-2 biased vaccine has the potential to reduce amyloid plaque burden while avoiding Th-1 mediated toxicity.

AβDT Conjugated Vaccines

Peptide Epitope Selection:

Targeting the Aβ B cell epitope(s) whilst avoiding the Aβ-specific T cell epitope(s) is a strategy pursued by some investigators to avoid some of the adverse effects seen in the AN1792 clinical trial with fibrillar, full length Aβ1-42. It has been shown that the Aβ1-15 sequence encodes relevant B cell epitopes (Geylis et al., 2005; Lemere et al., 2004; Lemere et al., 2000; McLaurin, et al., 2002; Agadjanyan et al., 2005). This sequence may be conjugated to immunogenic carriers to improve immunogenicity.

The data presented in FIGS. 1A, 1B and 2 show that when Aβ1-40 and Aβ1-42 are formulated in MAS-1 adjuvant or IFA adjuvant, these Aβ vaccines may induce Th2 dominated immune responses. Whereas, Aβ1-40 and Aβ1-42 formulated in CFA also induces a significant Th1 immune response which results in Th1 cell mediated inflammation as reported with Aβ1-40 and Aβ1-42 formulated in QS21 adjuvant in AN 1792 vaccine. Thus, based on these results, conjugated Aβ vaccines comprising Aβ epitope sequences derived from Aβ amino acid residues 16 through 40 and 16 through 42, when conjugated to a suitable immunogenic carrier may be expected to induce robust and safe Th2 dominated immune responses when formulated as MAS-1 or IFA based vaccines. Likewise, these constructs when formulated with alum, an approved Th2 biased adjuvant, may also be expected to produce Th2 dominated immune responses. These epitope sequences may typically contain from 7 to 15 consecutive amino acid residues derived from the Aβ sequences 1-40 and 1-42.

Immunogenic Carrier Selection:

Aβ1-15 peptide lacking helper T cell epitopes is poorly immunogenic when formulated in Th-2 biased alum adjuvant (Agadjanyan et al., 2005). This is likely to be the case for Aβ1-15 peptide formulated in MAS-1, since Aβ1-14 formulated in IFA has been shown to be a poor immunogen in guinea pigs unless extrinsic T cell help was provided by coupling to keyhole limpet hemocyanin (KLH) carrier protein or to foreign UBITh epitopes (Wang et al., 2007). Similarly, Aβ peptides comprising 7 to 15 amino acid residues derived from Aβ1-40 and Aβ1-42 are also predicted to be poorly immunogenic when formulated by themselves in IFA, MAS-1, or alum adjuvants.

The immunogenicity of short non-immunogenic peptides may generally be enhanced by coupling to Th epitopes such as synthetic PADRE constructs (Agadjanyan et al., 2005), or to immunogenic carrier proteins, e.g. mutant cholera B toxin (CBT), KLH, mutant diphtheria toxin (CRM), or to toxoids such as tetanus toxoid (TT) or diphtheria toxoid (DT), all of which contain Th epitopes to provide T cell help for IgG production and immunological memory. DT is chosen as the immunogenic carrier in this AD vaccine, because it has long been approved for use in childhood and adult vaccines and is available as a GMP compliant component. In one embodiment, the Aβ peptide epitope is conjugated to DT via a seven residue spacer sequence with a terminal cysteine residue via its sulfhydryl moiety using a bi-functional cross-linker. In other embodiments, the Aβ epitopes without the 7 residue spacer sequence but ending in a terminal cysteine residue may be conjugated via its sulfhydryl moiety to the immunogenic carrier. Alternative coupling chemistries well known in the art, such as carbodiimide chemistries, may also be used to effect the conjugation of Aβ epitopes to the immunogenic carrier.

Synthesis of Aβ15DT Conjugates:

The results indicate that immunogenicity may be affected by the peptide-to-carrier substitution ratio. The Aβ15 peptide sequence and the conjugation methods, are provided below. In summary, a 22 residue Aβ15-mer peptide is synthesized by solid-phase chemistry. Aβ15DT conjugates are prepared at two Aβ15 peptide:DT molar substitution ratios. The substitution ratios of the two Aβ15DT conjugates, determined by mobility on SDS-PAGE, are 7.6 (#1) and 21.1 (#2) (see Table 1). Conjugation ratios from about 5 moles to about 30 moles of peptide per mole of immunogenic carrier are useful for the compositions.

TABLE 1

Characterization of Aβ15DT Conjugates by SDS-PAGE

| | DT | Aβ15DT #1 | Aβ15DT #1 |
|---|---|---|---|
| Median MW | 55.1 kD | 75.6 kD | 111.8 kD |
| Molar Sub. Ratio (peptide:DT) | NA | 7.6 | 21.1 |

Immunopotency of Aβ15DT in MAS-1:

Both young DBA2 (6 wk-old; n=4/group) and aged C57BL/6 (12 mo-old; n=2/group) female mice are immunized with the conjugates at 100 µg doses in 0.1 mL MAS-1, s.c., on days 0, 14, 42, and 84. Blood samples are taken pre-immunization and at days 28, 56, and 98, and Aβ antibody titers are assayed by ELISA using Aβ1-42 peptide as target antigen. Results are presented in FIG. 4.

FIG. 4 shows an immunopotency in mice of Aβ15$_{(7)}$DT and Aβ15$_{(22)}$DT conjugates at peptide-to-carrier substitution ratios of 7 and 22, respectively, formulated in MAS-1. Aβ15DT conjugates are synthesized at peptide to DT substitution ratios of 7 and 22 moles/mole. The conjugates and Aβ1-42 are formulated in MAS-1 adjuvant and evaluated at 100 µg/0.1 mL s.c dose, injected on days 0, 14, 42 and 84, for immunopotency in 6 wk old DBA (n=4/group) and 12 mo old C57BL/6 (n=2/group) mice. Plasma Aβ antibodies are measured by ELISA against Aβ1-40.

Both Aβ15$_{(7)}$DT and Aβ15$_{(22)}$DT conjugates in MAS-1 induced rapid and potent antibody responses to Aβ measured by ELISA. Anti-Aβ titers continued to rise following further immunizations with Aβ15$_{(22)}$DT in MAS-1. The induction of anti-Aβ specific antibodies is significantly superior to that seen with Aβ1-42 in MAS-1, which in DBA strain mice are roughly 50 μg/mL on day 28 as shown in FIG. 1. At 28 days, both Aβ15DT conjugates generate anti-Aβ antibody levels more than 5 times greater than those generated with Aβ1-42 in MAS-1 in DBA mice. These results, confirm that Aβ15DT in MAS-1 is a highly effective immunogen, even in older C57BL/6 mice which are in general poorly immunoresponsive to Aβ peptides and, surprisingly, show that the potency of the immune response increased as the molar substitution ratio of epitope to immunogenic carrier was increased.

The results indicate that immunogenicity may be affected by the peptide-to-carrier substitution ratio, the dose, and the dose regimen. Both conjugates in MAS-1 induced predominantly Th-2 antibody isotypes (FIG. 5) that recognize the N terminal region of Aβ1-42 (FIG. 6), and bind to amyloid plaques in paraffin-embedded human AD brain tissue sections (FIG. 7).

FIG. 6 shows an epitope mapping of anti-Aβ specificity induced by Aβ1-42, Aβ15$_{(7)}$DT, and Aβ15$_{(22)}$DT in MAS-1. Epitope mapping conducted by inhibition ELISA using Aβ1-40 coating Ag wells and Aβ peptide fragments as inhibitors of mouse Ab binding. Similar Ab isotype and specificity results are obtained with DBA mice.

FIG. 3 shows an immunopotency in mice of Aβ15$_{(7)}$DT and Aβ15$_{(22)}$DT conjugates at peptide-to-carrier substitution ratios of 7 and 22, respectively, formulated in MAS-1. DA (6 wk-old; n=4/group) and aged C57BL/6 mouse (12 mo-old; n=2/group) female mice received 100 μg of each conjugate in 0.1 mL MAS-1 s.c. on days O and 14. Blood samples are taken pre-immunization and at Day 28 and Aβ antibody titres assayed by ELISA.

A 0.4:1 w/w mixture of Aβ15$_{(7)}$DT and Aβ15$_{(22)}$DT in MAS-1 elicited significant anti-Aβ Ab responses in 14 month old 3×Tg-AD mice (FIG. 8). These animals are immunized s.c with 4 doses of 100 ug Aβ15DT in 0.1 mL MAS-1 at 0, 2, 6, and 12 weeks and are euthanized at 16 weeks (i.e., at 18 months age). Splenocytes from immunized animals specifically responded to Aβ15DT, but not to full length Aβ1-40/42 demonstrating that immune tolerance to native Aβ was preserved (FIG. 9). Brain sections (6/mouse) from each animal from the Aβ15DT treated and MAS-1 placebo groups revealed a 74% reduction (p 0.0543 one-tailed Student's t Test) in amyloid plaque burden by Aβ15DT in MAS-1 compared with MAS-1 placebo. At 14 months age in 3×Tg-AD mice amyloid plaque deposition in the hippocampus is well established. Virtual absence of significant amyloid plaque in the vaccinated group demonstrates that immunization with Aβ15DT in MAS-1 resulted in a reduction in amyloid plaque and did not simply prevent further build up of amyloid plaque, indicating the potential utility for Aβ15DT/MAS-1 immunization to both prevent and treat Alzheimer's disease.

FIG. 8 depicts anti-Aβ levels in 3×Tg-AD mice. Two age matched groups of 3×Tg-AD mice (14 mo old; n=4/group; 3 M, 1 F) are immunized s.c. with 100 μg/0.1 mL comprised of a 0.4:1 w/w mixture of the Aβ15$_{(7)}$DT and Aβ15$_{(22)}$DT conjugates in MAS-1 or MAS-1 placebo at 0, 2, 6, 12, and 16 wk. Animals are euthanized after 17 weeks immunotherapy (Active18.5 and placebo 18.3 mo. age respectively). Anti-Aβ1-40 antibodies are determined by ELISA on blood samples collected at 0 (pre-immunization), 4, 8, and 16 wks.

These animals are immunized s.c with 4 doses of 100 ug Aβ15DT in 0.1 mL MAS-1 at 0, 2, 6, and 12 weeks and are euthanized at 16 weeks (i.e., at 18 months age). Splenocytes from immunized animals specifically responded to Aβ15DT, but not to full length Aβ1-40/42 demonstrating that immune tolerance to native Aβ are preserved (FIG. 9).

FIG. 9 shows a splenocyte stimulation assay. Two age matched groups of 3×Tg-AD mice (14 mo old; n=4/group; 3 M, 1 F) are immunized s.c. with 100 μg/0.1 mL comprised of a 0.4:1 w/w mixture of the Aβ15$_{(7)}$DT and Aβ15$_{(22)}$DT conjugates in MAS-1 or MAS-1 placebo at 0, 2, 6, 12, and 16 wk. Animals are euthanized after 17 weeks immunotherapy (Active18.5 and placebo 18.3 mo. age respectively).

Brain sections (6/mouse) from each animal from the Aβ15DT treated and MAS-1 placebo groups revealed a 74% reduction (p 0.0543 one-tailed Student's t Test) in amyloid plaque burden by Aβ15DT in MAS-1 compared with MAS-1 placebo. At 14 months age in 3×Tg-AD mice amyloid plaque deposition in the hippocampus is well established. Virtual absence of significant amyloid plaque in the vaccinated group demonstrates that immunization with Aβ15DT in MAS-1 results in a reduction in amyloid plaque and did not simply prevent further build up of amyloid plaque, indicating the potential utility for Aβ15DT/MAS-1 immunization to both prevent and treat Alzheimer's disease.

Immunogenicity and efficacy may be affected by any number of factors such as the peptide-to-carrier substitution ratio, the adjuvant, the formulation of the water-in-oil emulsion, the dose, and the dose regimen. This indicates that these factors must be assessed in order to optimise AD vaccine efficacy.

FIG. 10 depicts brain sections from each 3×Tg-AD Mouse stained for Aβ plaque shows significant reduction in hippocampal plaque burden in animals immunized with Aβ15DT conjugates in MAS-1, but not in animals immunized with MAS-1 placebo.

Our results indicate that immunogenicity and efficacy may be affected by any number of factors such as the peptide-to-carrier substitution ratio, the adjuvant, the formulation of the water-in-oil emulsion, the dose, and the dose regimen. This indicates that these factors must be assessed in order to optimise AD vaccine efficacy.

The Water-in-Oil Emulsion Adjuvant/Delivery System

Many factors, such as antigen, adjuvant, and delivery systems may be modified to elicit specific cellular and humoral immune responses. The data show that the Aβ1-42 formulated in a water-in-oil adjuvant delivery system such as MAS-1 induces a significant humoral antibody response in naive mice with a predominantly Th2 bias (IgG1 and lgG2b isotypes) (FIGS. 1 and 2).

However, short Aβ fragments, while potentially avoiding an Aβ-specific cellular immune response, are poorly immunogenic. Conjugation of small molecules, including peptides, to immunogenic carriers such as DT is an established means of enhancing immunogenicity, but even DT conjugated self epitopes may require a Th-2 biased adjuvant with superior potency than alum adjuvant in order to be effective therapeutically. A water-in-oil adjuvant emulsion such as MAS-1 may induce robust Th2 biased immune responses to Aβ15DT conjugated self antigens while having the potential to avoid Th1 biased cell mediated inflammatory side effects that have limited the effectiveness of previous attempts to develop and Aβ15DT vaccine for Alzheimer's disease.

In one example, the components of the oil adjuvant vehicle suitable for use in the compositions, comprise a first sugar ester emulsifier such as mannide monooleate (MMO) or sorbitan monooleate, a second emulsifier such as a hydrogenated castor oil, for example, polyoxyl-40-hydrogenated castor oil (POCO), and naturally occurring and metabolizable oils, preferably squalene and squalane. The metabolizable oils typically comprise from about 85% to about 90% by weight of the oil, the first sugar ester emulsifier from about 9% to about 12% by weight of the oil, and the second emulsifier from about 0.5% to about 0.7% by weight of the oil. In one example, the metabolizable oil component is typically 50% squalene, 50% squalane by weight, but the concentration of these components may vary within this component. A suitable adjuvant vehicle for use in the compositions is MAS-1, which is comprised of naturally occurring and metabolizable components derived from vegetable sources, and is commercially available from Mercia Pharma, Inc, Scarsdale, N.Y. (www.merciapharma.com).

The components of the oil vehicle, including their starting materials, may be derived from either animal or vegetable sources, or combinations thereof, are all commercially available from multiple sources. Suitable sugar esters as the first emulsifier in addition to MMO include polysorbates, particularly sorbitan monooleate. In addition to POCO as the second emulsifier, sorbitan esters, such as sorbitan monopalmitate, polysorbates, such as the Tweens family of emulsifiers, and Hypermers B239 and B246 may be useful.

In one example, the nanoparticulate vaccine emulsions disclosed typically contain from about 65% by weight to about 75% by weight of the adjuvant oil vehicle and from about 25% to about 35% by weight of an aqueous phase containing the protein antigen. In certain embodiments of the compositions, the aqueous phase comprises from about 27% to about 33% by weight of the vaccine emulsion.

The water-in-oil vaccine emulsions used in the compositions, in one example, may be formulated so that the aqueous globules in the emulsion carrying the antigen have median diameters less than 1 micron with median diameters in the range from about 100 nanometers to about 1 micron, and typically with an average diameter of about 300 nanometers. In one example, the oil components of the adjuvant are preferably naturally occurring biological oils that are metabolizable, unlike the mineral oil that comprises the oil phase of the well known Freund's adjuvants (both incomplete and complete formulations).

The disclosed vaccine emulsions may tolerate high concentrations of antigen (up to at least 10 mg/mL) and should be compatible with commonly used protein solubilizers (e.g., 4M urea, 30% DMSO). Unlike IFA emulsions, in one example, they should be compatible with aqueous phases having a wide range of pH (3-8), and be unaffected over a wide range salt concentrations. Unlike IFA emulsions (>1, 500 cP), the vaccine emulsions in one example, should have a low viscosity (<100 cP) as free flowing emulsions permitting high precision low volume (0.1 mL) dosing. The physico-chemical characteristics of the disclosed vaccine emulsions, in one example, should have a median distribution of globule size diameter of (D(v,0.5)) less than or equal to 1.0 μm, and be unaffected by high concentrations of protein in the aqueous phase.

Animal Models for Evaluating the Immunogenic Compositions

Gene-targeted and transgenic mice are a valuable tool for modeling various aspects of AD pathology, although no mouse model fully reproduces its entire neuropathology. The 3×Tg-AD mice develop both plaques composed of Aβ peptide, and neurofibrillary tangle composed of hyperphosphorylated Tau protein in relevant brain regions, with associated age-dependent decline in the cognitive phenotype in both spatial and contextual learning and memory paradigms. Thus, they provide a valuable model for evaluating potential AD therapeutics (Oddo et al., 2003).

The peptide immunogen Aβ1-2 has been shown to elicit therapeutic anti-Aβ antibodies in preclinical and clinical studies and Aβ1-42 in MAS-1 induces Th2 biased anti-Aβ antibodies that recognize amyloid plaques in brain tissue slices.

3×Tg-AD triple transgenic mice, express human mutant APP, tau and presenilin 1. These mice originated on a C57BL/6/1295 background but have been backcrossed for many generations onto C57BL/6 mice, resulting in very little 129 genotype remaining. They are homozygous, easy to breed and progressively develop AB and tau pathology with a temporal and regional specific profile that closely mimics pathological development in the human AD brain. Aβ deposition develops in these mice before the tau pathology, which is consistent with the amyloid cascade hypothesis, which stipulates that Aβ is the trigger and that tau pathology is a downstream consequence of Aβ pathology (Hardy and Selkoe, 2002).

In order to further evaluate the disclosed immunotherapeutic compositions, one may immunize 3×Tg-AD mice at 6 months (young/prevention) and 14 months of age (old/treatment) by s.c. injections with the optimal dose determined form dose ranging dose regimen studies with Aβ1-15:DT optimized for peptide to carrier substitution ratio. The mice may be immunized for nine months in the preventative study and for 5-6 months in the treatment study. A group of mice vaccinated with Aβ1-42 in MAS-1 could be included as positive control and a negative control group immunized with DT in the selected adjuvant or W/O placebo adjuvant, in both prevention and treatment studies. Due to the variability in the behavioral component of the study, group sizes of 16 3×Tg-AD mice will be required.

Behavioral testing using the Morris Water Maze, in one example, should be conducted at the end of each study. Spatial learning may be measured by latency and distance to platform, while memory retention may be measured by probe trials, although correlations between behavioral performance and amyloid plaque deposition are well established in 3×Tg-AD mice.

Immunization of 3×Tg-AD mice with Aβ15DT in MAS-1 lead to a robust Th-2 dominated humoral immune response, avoiding Th-1 dominated immunity and the potential for inducing cell-mediated inflammatory changes in the brain. The induction of Aβ specific regulatory T cells by the compositions of the invention should further reduce the potential for cell mediated inflammatory side effects. The antibodies generated lead to a decrease of Aβ in the brain which should correlate with improvement in cognitive function in mice. It was expected that immunizing mice after they have accumulated cerebral Aβ (14 months) would only partially lower plaque burden, since it is well recognized that older 3×Tg-AD mice typically express a less robust immune response whereas, in fact, potent Th-2 dominant humoral immune responses and concomitantly statistically significant reductions in hippocampal plaque burden without evidence for microhemorrhage, are seen.

In the three autopsy cases from the AN1792 clinical trial, extensive vascular Aβ remained despite parenchymal Aβ clearance, and one of these had numerous brain microhemorrhages (Nicoll et al., 2003; Ferrer et al., 2004; Maliash et al., 2005). In evaluating the immunotherapeutic compositions one should play close attention to the appearance of cerebral microhemorrhage as this has also been observed following passive immunization of mice with Aβ monoclonal antibodies (Pfeifer et al., 2002, Wilcock et al., 2004, Racke et al., 2005; Lee et al., 2005). These microhemorrhages are believed to be caused by the overly rapid clearance of Aβ parenchymal deposits and their subsequent vascular deposition by the high doses of high affinity mAbs, as well as possibly by the binding of Aβ mAbs with Aβ in the microvasculature.

In general, active immunization in mice has not been associated with the development of cerebral microhemorrhage, except for a recent report showing that active immunization of APP+PS1 transgenic mice with Aβ1-42 formulated in CFA/IFA was associated with an increase in microhemorrhages (Wilcock et al., 2007). A recent study by Asuni et al., (2006) showed that vaccination of Tg2576 'mice with an Aβ derivative in alum, an adjuvant favoring a Th2 response, reduced Aβ burden without any evidence for microhemorrhages. Thus, unlike in the case of Aβ1-42 in QS21 based adjuvant (AN1792), or other Th-1 biased adjuvant formulations used to promote robust immune responses to Aβ, the results observed herein with Aβ1-42 in MAS-1 or Aβ15DT in MAS-1 in 3×Tg-AD mice, predict that these compositions are suitable as therapeutic vaccines for early prevention and treatment of Alzheimer's disease and are expected to induce significantly more robust, Th-2 dominated immune responses avoiding the potential for Th-1 mediated cytotoxicity or breaking immune self tolerance to the endogenous target while reducing or preventing amyloid plaque deposition and having the potential to reduce the consequent development of hyperphosphorylated Tau protein.

Materials and Methods

Aβ1-42 Peptide:

The 42 residue peptide may be manufactured using solid phase synthesis. The sequence of this peptide is shown below:

DAEFR$^5$HDSGY$^{10}$EVHHQ$^{15}$KLVFF$^{20}$AEDVG$^{25}$ SNKGA$^{30}$IIGLM$^{35}$VGGVV$^{40}$IA$^{42}$ (SEQ ID NO: 1)

Aβ Peptide Epitopes:

The 22 residue 15-mer Aβ peptide immunomimic peptides with a 7 amino acid residue peptide spacer (XXXXXXC-COOH) may be manufactured using solid phase synthesis. The sequences of the 15-mer Aβ1-15, Aβ16-30, Aβ21-35, and Aβ31-42 are shown below:

```
                                            (SEQ ID NO: 2)
NH2-D¹AEFR⁵HDSGY¹⁰EVHHQ¹⁵X: XXXXXXC-COOH (SEQ ID NO: 3)
NH2-K¹⁶LVFF²⁰AEDVG²⁵SNKGA³⁰ XXXXXXC-COOH (SEQ ID NO: 4)
NH2-A²¹EDVG²⁵SNKGA³⁰IIGLM³⁵ XXXXXXC-COOH (SEQ ID NO: 5)
NH2-I³¹IGLM³⁵VGGVV⁴⁰IA⁴²XXXXXXC-COOH
```

Various spacer peptides are known to those skilled in the art and these and other peptide sequences may be used in the invention. U.S. Pat. Nos. 5,023,077, 5,468,494, and 5,688,506 and the disclosures of which are hereby incorporated by reference, describe useful peptide spacer sequences that may be used in the disclosed compositions. Wherein the peptide spacer sequences incorporated from the aforementioned patents are as follow:

```
                          (SEQ ID NO: 6)
Arg-Pro-Pro-Pro-Pro-Cys-;

(SEQ ID NO: 7)
Ser-Ser-Pro-Pro-Pro-Pro-Cys-;

(SEQ ID NO: 8)
Cys-Pro-Pro-Pro-Ser-Ser-;

(SEQ ID NO: 9)
Arg-Cys-Pro-Pro-Pro-Pro-Arg-;
```

AβDT Conjugates:

Methods of conjugating peptides to immunogenic carrier proteins are well known to those skilled in the art, for example U.S. Pat. Nos. 5,468,494, 5,688,506 and 6,359,116 the disclosure of which are hereby incorporated by reference.

Aβ1-15 Peptide Synthesis and Aβ15DT Conjugation:

The 22 mer peptide comprising Aβ residues 1-15 may be coupled to DT using maleimide-NHS ester bifunctional cross-linking chemistry. The peptide via its C-terminal CySH residue may be coupled to DT carrier by bifunctional cross-linking agents well known to those skilled in the art, for example, epsilon-maleimidocaproic acid N-hydroxysuccinimide ester (eMCS) crosslinker, and related bifunctional analogs (Sulfo-eMCS). This mechanism of coupling has been selected because it is highly specific. The DT is first activated with eMCS under pH conditions enabling reaction of the succinimidyl moiety of the linker to free amino groups on DT to produce maleimido-activated DT (MDT). Once complete, unreacted eMCS and its degradation products are removed and activation buffer exchanged for coupling buffer optimal for reaction of the free sulfhydryl of the peptide with the maleimido group of MDT to conjugate the peptide to the carrier. The conjugate is then purified and analyzed. Selection of the proper eMCS: DT ratio and activation/coupling conditions result in consistent peptide: carrier substitution ratios at both laboratory and production batch scales. Each conjugate may be characterized by analytical methods. The peptide: carrier molar substitution ratio may be determined by quantitative amino acid analysis and/or by mobility on SDS-PAGE.

Conjugate purity may be assessed by SEC HPLC and by SDS PAGE. Conjugate identity may be tested by Western Blot utilizing additional samples of gel from the SDS PAGE and by amino acid analysis.

Aβ1-15BSA Conjugate:

Aβ1-15 epitope, without the spacer sequence but with a C-terminal Cys residue, is conjugated to BSA, for use as the target antigen in ELISA for the measurement of peptide specific antibodies. Alternatively, Aβ1-15 peptide, or longer peptides of Aβ starting from the N terminus and including residues up through residue 42, may serve as target antigens in the ELISA.

Animal Immunizations:

Mice are injected subcutaneously (s.c.) into the scruff of the neck or hind limb flanks, or intraperitoneally (i.p.), with 100 μl of immunogen, by well known methodology.

Blood and Tissue Collection:

Mice are bled from the tail vein prior to and during the immunization period, and serum prepared and frozen at −20° C. For collection of larger volumes of serum, mice are terminally bled by cardiac puncture at the end of the experiment and serum prepared as above and used as a reference standard for experiments. 3×Tg-AD mice are euthanized by $CO_2$ inhalation and pericardially perfused with saline. The brains are removed and divided in half along the midline. One hemibrain is snap-frozen in liquid nitrogen and stored at −80° C. for biochemical studies (e.g., Aβ ELISAs). The other hemibrain is either drop-fixed in 4% paraformaldehyde in PBS for 2 hr at RT, sucrose protected in 10-30% sucrose at 4° C. and embedded in OCT (TissueTek) for cryosectioning or, drop-fixed in 10% neutral buffered formalin for 2 hr at RT, washed in TBS, dehydrated, cleared of lipids (Histoclear), and embedded in paraffin for paraffin sagittal sectioning. Six-to-ten micron sagittal cryosections and 12-micron paraffin serial sections are cut and stored for staining. Spleen tissue for proliferation and cytokine analyses are removed under sterile conditions.

Mouse Splenocyte Proliferation Assay:

Splenocytes are prepared by centrifugation of a single cell suspension on Lympholyte-M (Cederlane, Homby, ON, Mayada). Splenocytes, at a concentration of $2\times10^6$/ml, are cultured in RPMI supplemented with 10% FBS and stimulated with A$\beta$1-15, A$\beta$1-42, and DT and A$\beta$15DT (0-50 µg/ml) in 96 well plates. Conmayavalin A is used as a positive control to ensure the viability of the cells. Culture supernatants are harvested for cytokine ELISAs at 48 hr. After 72 hr in culture, 1 µCi [3H] thymidine is added to each well and the cells cultured for an additional 18 hr. The cells are harvested using a plate washer and the radioactivity measured using a liquid scintillation counter. A stimulation index (SI) is calculated using the following formula: counts per minute (CPM) with peptide antigen/CPM with no antigen.

Measurement of anti AB antibodies in Mouse Sera by ELISA:

Plates are coated with normal mouse IgG (standard curve) and 2 µg/ml A$\beta$1-42 peptide and incubated overnight at 4° C. Plates are then blocked in 5% goat serum, 1% BSA, and 0.005% Tween-20 for 2 hours at RT. Following washing, dilutions of mouse sera is added to the wells and incubated for 2 hours at RT. Goat anti-mouse conjugated to HRP (Kirkegaard and Perry Laboratory, Gaithersburg, Md.) is used as secondary antibody and incubated on plates for 1 hour at RT. Following addition of the color substrate, 3,3',5.5'-Tetramethylbenzidine (TMB) for 30 min the reaction is stopped with 0.5M HCl and the plates read on a plate reader at 450 nm. Isotype Analysis: Quantitative isotype specific ELISAs are performed using isotype specific secondary antibodies for IgG1, IgG2a, IgG2b, IgA and IgM (Zymed, San Francisco, Calif.) and the addition of a standard curve of the appropriate isotype (Southern Biotechnology, AL) to the standard ELISA described above.

Detection of A$\beta$ Plaques in Human and Mouse Brain:

Sera from immunized and control mice are diluted serially 1:100 to 1:10,000 and applied to human AD and J20APP transgenic mouse brain sections for immunohistochemical detection of plaques and vascular amyloid. Biotinlyated goat anti-mouse secondary antibody is used together with the ABC ELITE HRP standard (A and B) and reacted with DAB for visualization. Adjacent sections are labeled with AB antibodies such as R1282 (generic AB polyclonal, Selkoe lab) or 6E10 (monoclonal A$\beta$1-17, Covance Research Products, Dedham, Mass.).

A$\beta$ Protein ELISA: Both soluble and insoluble A$\beta$40 and A$\beta$42 levels in the brain are determined by ELISA kits (Signet) according to the manufacturer's instructions (Covance Research Products, Inc, Berkeley, Calif.). Snap frozen whole hemispheres are homogenized in 4 volumes of PBS containing protease inhibitor cocktail (Roche, Indianapolis, Ind.). Homogenates are spun at 100×g for 30 min at 4° C. Supernatants are analyzed for soluble A$\beta$ levels by ELISA. The PBS·pellet are re-suspended in 10 volumes of guanidine buffer (5M guanidine HCL, 50 mM Tris pH 8.0). Samples are mixed for 4 hr at RT. Brain homogenates are then diluted 1:10 in casein buffer (0.25% casein, 5 mM EDTA, protease inhibitor cocktail in PBS), mixed, and spun at 16,000×g for 20 minutes. Additional dilutions are made in 0.5 M guanidine buffer with 0.1% BSA and insoluble A$\beta$ levels measured by ELISA Immunohistochemistry, Histology, and Image Analysis:

Immunohistochemistry are performed using the ELITE ABC method of Vector Laboratories (Burlingame, Calif.) and DAB as the chromagen. Briefly, paraffin sections are deparaffinized in Histoclear (National Diagnostics, Atlanta, Ga.) and rehydrated in graded ethanols to water. Cryosections are thawed, air-dried for 15 min, and washed gently in TBS. From this point on, the staining procedure are the same for both paraffin sections and cryosections. Endogenous methanol is quenched, sections are blocked in 10% serum in TBS, and sections incubated in primary antibody overnight at 4° C.

Sections are then washed in TBS, incubated in biotinylated secondary antibody (Vector Labs) for 30 min at RT, washed in TBS, incubated in avidin-HRP complex (Vector Labs) for 30 min at RT and then developed in DAB.

Sections are counterstained in hematoxylin (unless designated for image analysis), dehydrated, cleared and coverslipped with Permount (Fisher). Double immunofluorescence are performed by blocking in 2% serum, mixing 2 primary antibodies (MoAb and PAb) and applying to sections overnight at 4° C., rinsing in 0.1 M Tris, blocking in 2% serum in Tris, mixing two fluorescently-labeled secondary antibodies and applying to sections for 2 hr at RT, rinsing twice in Tris, incubating the sections in 0.3% Sudan Black B in 70% ethanol in the dark for 10 min, washing in TBS, washing in water, fixing in formalin for 1 hr in the dark, washing in water, and coverslipping the slides with Hydromount non-fluorescing aqueous media (National Diagnostics, Atlanta).

Coverslips are sealed with clear nail-polish to prevent drying. Negative controls for IHC and IF included omission of primary antibody or using mouse IgG as primary antibody. The primary antibodies for immunohistological detection of A$\beta$ and markers of inflammation are listed below.

Primary Antibodies for Immunohistochemistry:

A$\beta$ (R1282, Dr. Selkoe, Brigham and Women's Hospital, Boston); A$\beta$40, A$\beta$42 and 6E10 (BioSource and Covance Research Products), Glial fibrillary acidic protein (GFAP) Mab (Dako, Denmark), microglia/macrophage Mab [CD45 (Serotec), CD11b/Mac-1 (Serotec), MHC II (PharMingen), F4/80 (Serotec), FcgR II-CD16 and II-CD32 (PharMingen)], B cells (CD40, Novacastra Laboratories, UK), T cells (CD5, CD3; Serotec), APP Mab (IG6, Covance Research Products); phospho-tau (ATB, Innogenetics), mouse 1g (goat anti-mouse IgG).

Histological Staining:

Thioflavine S staining to detect fibrillar A$\beta$ protein in brain sections are performed by incubating slides in a 1% aqueous solution of Thioflavine S for 10 min followed by rinses in 80 and 95% ethanol, and then distilled water. Haemosiderin staining to detect microhemorrhages are performed by incubating hydrated sections in 2% ferrocyanide in 2% hydrochloric acid for 15 min. Hematoxylin and eosin (H&E) staining are used to assess mononuclear cell infiltration in brain, lung, heart, liver and spleen sections.

Quantitative Image Analysis:

Computer-assisted quantification of A$\beta$ plaque burden and gliosis are performed using IP Lab Spectrum 7.1 Image Analyzer (Fairfax, Va.) as previously described (Weiner et al., 2000). Four-to-eight sagittal images of immunolabelled sections are captured at equi-distant levels (~100 µm apart) through each mouse brain using a Nikon microscope with a Leica motorized stage and a SPOT camera. All images for one experiment are captured on the same day with the threshold being held constant throughout the image analysis.

The percent area occupied by immunoreactivity (above threshold) is calculated.

Alternative combinations and variations of the examples provided will become apparent based on this disclosure. It is not possible to provide specific examples for all of the many possible combinations and variations of the embodiments described, but such combinations and variations may be claims that eventually issue.

The invention claimed is:

1. An immunotherapeutic composition for the treatment of Alzheimer's disease comprising:
   an immunogen comprising a peptide comprising an amino acid sequence of 7-15 consecutive amino acid residues of human amyloid beta 1-15 peptide (SEQ ID NO: 2) conjugated to an immunogenic carrier protein, formulated in a water-in-oil emulsion with an oily adjuvant vehicle comprising squalene, squalane and mannide monooleate, and polyoxyl-40-hydrogenated castor oil, wherein the immunogen is contained within aqueous globules that have a median diameter from about 100 nanometers to about 1 micron;
   wherein:
   the immunogenic carrier protein is diphtheria toxoid carrier;
   the immunogen has a conjugation ratio of moles of peptide per mole of carrier of from about 5:1 to about 30:1;
   the oily adjuvant vehicle comprises from about 85% to about 90% squalene and squalane, from about 9% to about 12% mannide monooleate and from about 0.5% to about 0.7% polyoxyl 40-hydrogenated castor oil; and
   the peptide comprising the amino acid sequence of human amyloid beta protein is coupled to the immunogenic carrier protein via a spacer.

2. The composition of claim 1 wherein the average aqueous globule diameter is about 300 nanometers.

3. The composition of claim 1, wherein the water-in-oil emulsion comprises from about 65% to about 75% oily globules containing the immunogen.

4. The composition of claim 1, wherein the squalene and squalane are in a 50/50 ratio by weight.

5. The composition of claim 4, wherein the oily adjuvant vehicle is Mercia Adjuvant System (MAS-1).

6. The composition of claim 1, wherein the spacer is a peptide spacer.

7. The immunotherapeutic composition of claim 1, wherein the immunogen has a conjugation ratio of moles of peptide per mole of carrier of 7:1.

8. The immunotherapeutic composition of claim 1, wherein the immunogen has a conjugation ratio of moles of peptide per mole of carrier of 22:1.

9. The immunotherapeutic composition of claim 1, wherein the immunogen has a conjugation ratio of moles of peptide per mole of carrier of 22:1 within the range of about 5:1 to about 25:1.

10. The immunotherapeutic composition of claim 1, comprising a plurality of immunogens according to claim 1, said immunogens having conjugation ratios of moles of peptide per mole of carrier within the range of about 5:1 to about 25:1.

11. A method of treating or reducing amyloid plaque deposition in Alzheimer's disease in a human patient, which comprises administering to the patient the immunotherapeutic composition of claim 1.

* * * * *

```
                        SEQUENCE LISTING

<160> NUMBER OF SEQ ID NOS: 9

<210> SEQ ID NO 1
<211> LENGTH: 42
<212> TYPE: PRT
<213> ORGANISM: Homo sapiens

<400> SEQUENCE: 1

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val Ile Ala
        35                  40

<210> SEQ ID NO 2
<211> LENGTH: 15
<212> TYPE: PRT
<213> ORGANISM: Homo sapiens

<400> SEQUENCE: 2

Asp Ala Glu Phe Arg His Asp Ser Gly Tyr Glu Val His His Gln
1               5                   10                  15

<210> SEQ ID NO 3
<211> LENGTH: 15
<212> TYPE: PRT
<213> ORGANISM: Homo sapiens

<400> SEQUENCE: 3

Lys Leu Val Phe Phe Ala Glu Asp Val Gly Ser Asn Lys Gly Ala
1               5                   10                  15

<210> SEQ ID NO 4
<211> LENGTH: 15
<212> TYPE: PRT
<213> ORGANISM: Homo sapiens

<400> SEQUENCE: 4

Ala Glu Asp Val Gly Ser Asn Lys Gly Ala Ile Ile Gly Leu Met
1               5                   10                  15

<210> SEQ ID NO 5
<211> LENGTH: 12
<212> TYPE: PRT
<213> ORGANISM: Homo sapiens

<400> SEQUENCE: 5

Ile Ile Gly Leu Met Val Gly Gly Val Val Ile Ala
1               5                   10

<210> SEQ ID NO 6
<211> LENGTH: 6
<212> TYPE: PRT
<213> ORGANISM: Artificial Sequence
<220> FEATURE:
<223> OTHER INFORMATION: Peptide Spacer
```

```
<400> SEQUENCE: 6

Ala Pro Pro Pro Pro Cys
1               5

<210> SEQ ID NO 7
<211> LENGTH: 7
<212> TYPE: PRT
<213> ORGANISM: Artificial Sequence
<220> FEATURE:
<223> OTHER INFORMATION: Peptide Spacer

<400> SEQUENCE: 7

Ser Ser Pro Pro Pro Pro Cys
1               5

<210> SEQ ID NO 8
<211> LENGTH: 7
<212> TYPE: PRT
<213> ORGANISM: Artificial Sequence
<220> FEATURE:
<223> OTHER INFORMATION: Peptide Spacer

<400> SEQUENCE: 8

Cys Pro Pro Pro Pro Ser Ser
1               5

<210> SEQ ID NO 9
<211> LENGTH: 7
<212> TYPE: PRT
<213> ORGANISM: Artificial Sequence
<220> FEATURE:
<223> OTHER INFORMATION: Peptide Spacer

<400> SEQUENCE: 9

Ala Cys Pro Pro Pro Pro Ala
1               5
```